(12) United States Patent
Iovannisci et al.

(10) Patent No.: US 7,811,765 B2
(45) Date of Patent: Oct. 12, 2010

(54) METHODS AND COMPOSITIONS FOR DETERMINING PREDISPOSITION TO INFLAMMATION-MEDIATED CARDIOVASCULAR DISEASE

(75) Inventors: David M. Iovannisci, Oakland, CA (US); Edward J. Lammer, Oakland, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 0 days.

(21) Appl. No.: 11/871,082

(22) Filed: Oct. 11, 2007

(65) Prior Publication Data

US 2008/0166721 A1 Jul. 10, 2008

Related U.S. Application Data

(60) Provisional application No. 60/851,396, filed on Oct. 12, 2006.

(51) Int. Cl.
*C12Q 1/66* (2006.01)
*C12P 19/34* (2006.01)

(52) U.S. Cl. .......................................... 435/6; 435/91.1

(58) Field of Classification Search ....................... None
See application file for complete search history.

(56) References Cited

U.S. PATENT DOCUMENTS

| | | | |
|---|---|---|---|
| 6,316,196 | B1 | 11/2001 | Morten |
| 6,576,753 | B1 | 6/2003 | Lam et al. |
| 6,939,674 | B2 | 9/2005 | Anderson et al. |
| 2003/0224418 | A1 | 12/2003 | Braun et al. |
| 2004/0209288 | A1 | 10/2004 | Mehrabian et al. |
| 2005/0113408 | A1 | 5/2005 | Helgadottir et al. |
| 2006/0019269 | A1 | 1/2006 | Helgadottir et al. |

OTHER PUBLICATIONS

Back et al. (Arterioscler. Thromb. Vasc. Biol., 2008, vol. 28, pp. 805-806).*
Hattersley et al. (Lancet, 2005, vol. 366, pp. 1315-1323).*
Ionnidis (Plost Med, 2005, 2(8):e124).*
Kroese et al. (Genetics in Medicine, vol. 6 (2004), p. 475-480).*
LTC4S Gene, Leukotriene C4 Synthase, Genecard, pp. 1-12, printed Dec. 21, 2008, available at www.genecards.org.*
Dwyer, J.,et al. Arachidonate 5-lipoxygenase promoter genotype, dietary archidonic acid, and atherosclerosis. New England Journal of Medicine. 2004, vol. 350, pp. 29-37.
Helgadottir, A., et al. The gene encoding 5-lipoxygenase activating protein confers risk of myocardial infarction and stroke. Nature Genetics. 2004, vol. 36, No. 3, pp. 233-239.
Helgadottir, A., et al. Association between the gene encoding 5-lipoxygenase-activating protein and stroke replicated in a Scottish population. Am J Hum Genet. 2005, vol. 76, pp. 505-509.
Helgadottir, A., et al. A variant of the gene encoding leukotriene A4 hydrolase confers ethnicity-specific risk of myocardial infarction. Nature Genetics. 2006, vol. 38, No. 1, pp. 68-74.
Mehrabian, M., et al. Identification of 5-lipoxygenase as a major gene contributing to atherosclerosis susceptibility in mice. Circulation Research. 2002, vol. 91, pp. 120-126.
Mehrabian, M., et al. Response to arachidonate 5-lipoxygenase variants in atherosclerosis, obesity, and bone trials. Circulation Research. 2006, vol. 98, pp. e68.

* cited by examiner

*Primary Examiner*—Sarae Bausch
(74) *Attorney, Agent, or Firm*—Shweta Chandra; Bozicevic, Field & Francis, LLP

(57) ABSTRACT

The present invention provides methods and compositions for detecting a predisposition to an inflammation-mediated cardiovascular disease in a human subject by detecting a level of leukotriene C4 synthase (LTC4S) gene product in a sample from a human subject indicative of a predisposition to an inflammation-mediated cardiovascular disease or detecting the presence or absence of an allele of LTC4S indicative of a predisposition to an inflammation-mediated cardiovascular disease. In addition, the present invention also provides kits for practicing the methods.

12 Claims, 2 Drawing Sheets

A.

B.

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
aagccaaagg cactgggaag                                                    20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
acatcatgct ggagccagcc                                                    20

<210> SEQ ID NO 3
<211> LENGTH: 21
<212> TYPE: DNA
<213> ORGANISM: Artificial Sequence
<220> FEATURE:
<223> OTHER INFORMATION: Probe

<400> SEQUENCE: 3
ggatggggac agggaacaga t                                                  21

<210> SEQ ID NO 4
<211> LENGTH: 20
<212> TYPE: DNA
<213> ORGANISM: Artificial Sequence
<220> FEATURE:
<223> OTHER INFORMATION: Probe

<400> SEQUENCE: 4
gatggggacc gggaacagat                                                    20
```

METHODS AND COMPOSITIONS FOR DETERMINING PREDISPOSITION TO INFLAMMATION-MEDIATED CARDIOVASCULAR DISEASE

CROSS-REFERENCE TO RELATED APPLICATIONS

This application claims priority benefit to U.S. provisional application Ser. No. 60/851,396, filed Oct. 12, 2006, which application is incorporated herein by reference in its entirety.

GOVERNMENT RIGHTS

This invention was made with government support under federal grant nos. R01 HL61357, R01 HL48050, and R01 HL54730 awarded by the National Institutes of Health. The United States Government has certain rights in this invention.

BACKGROUND OF THE INVENTION

Cardiovascular disease is a major health risk throughout the industrialized world. Atherosclerosis, the most prevalent of inflammation-mediated cardiovascular diseases, is the principal cause of heart attack, stroke, and gangrene of the extremities, and thereby the principle cause of death in the United States. Atherosclerosis is a complex disease involving many cell types and molecular factors. The process, in normal circumstances, is a protective response to insults to the endothelium and smooth muscle cells (SMCs) of the wall of the artery, consists of the formation of fibrofatty and fibrous lesions or plaques, preceded and accompanied by inflammation. The advanced lesions of atherosclerosis may occlude the artery concerned, and result from an excessive inflammatory-fibroproliferative response to numerous different forms of insult. For example, shear stresses are thought to be responsible for the frequent occurrence of atherosclerotic plaques in regions of the circulatory system where turbulent blood flow occurs, such as branch points and irregular structures.

Atherosclerosis is thought to also involve inflammation, because certain white blood cells—lymphocytes, monocytes, and macrophages—are present throughout the development of atherosclerosis. These cells usually gather only when inflammation develops. Atherosclerosis begins when monocytes are activated and move out of the bloodstream into the wall of an artery. There, they are transformed into foam cells, which collect cholesterol and other fatty materials. In time, these fat-laden foam cells accumulate and form atheromas in the lining of the artery's wall, causing a thickening and hardening of the wall. Atheromas may be scattered throughout medium-sized and large arteries, but usually form where the arteries branch—presumably because the constant turbulent blood flow at these areas injures the artery's wall, making these areas more susceptible to atheroma formation.

The deposition for cardiovascular disease, such as atherosclerosis, is slow and starts at an early age. Clinical symptoms may take years to manifest themselves and are very serious, including coronary heart disease and stroke. Generally, the disease process will have begun long before these clinical manifestations appear. Therefore it is desirable to have available a diagnostic technique which provides an early warning of the onset of the deposition for cardiovascular disease, such as atherosclerosis.

Relevant Literature

U.S. Pat. Nos. 6,316,196, 6,576,753, 6,939,674; U.S. Patent Application Publication Nos. 2003/0224418, 2004/0209288 2006/0019269, and 2005/0113408; Helgadottir et al., A. J. Human Genetics 76:505-509 (2005); Helgadottir et al., Nature Gentetics 36:233-239 (2004); Helgadottir et al., Nature Genetics 38(1):68-74 (2006); Mehrabian et al., Circ Res. 98(9):e68 (2006); Mehrabian et al., Circ Res. 91(2): 120-6 (2002); and Dwyer et al., N Engl J Med. 350(1):29-37 (2004).

SUMMARY OF THE INVENTION

The present invention provides methods and compositions for detecting a predisposition to an inflammation-mediated cardiovascular disease in a human subject by detecting a level of leukotriene C4 synthase (LTC4S) gene product in a sample from a human subject indicative of a predisposition to an inflammation-mediated cardiovascular disease or detecting the presence or absence of an allele of LTC4S indicative of a predisposition to an inflammation-mediated cardiovascular disease. In addition, the present invention also provides kits for practicing the methods.

The invention provides a method of detecting a predisposition to an inflammation-mediated cardiovascular disease in a human subject, by detecting a level of leukotriene C4 synthase (LTC4S) gene product in a sample from a human subject, wherein an increased level of LTC4S gene product as compared to a reference level known to be associated with a non-risk of development of an inflammation-mediated cardiovascular disease indicates that the human subject has a predisposition to an inflammation-mediated cardiovascular disease.

In some embodiments, the gene product is nucleic acid. In further embodiments, the detecting step includes a polymerase chain reaction or hybridization. In some embodiments, the gene product is a polypeptide. In further embodiments, the detecting is by immunoassay. In some embodiments, the inflammation-mediated cardiovascular disease is atherosclerosis. In some embodiments, the human subject is a female human subject.

The invention also provides a method of detecting a predisposition to an inflammation-mediated cardiovascular disease in a human subject, by detecting the presence or absence of an allele of a leukotriene C4 synthase (LTC4S) indicative of a predisposition to an inflammation-mediated cardiovascular disease, wherein the presence of the allele indicates the human subject has a predisposition to an inflammation-mediated cardiovascular disease.

In some embodiments, the detecting includes determining the subject's LTC4S promoter region genotype. In certain embodiments, the allele of LTC4S indicative of a predisposition to an inflammation-mediated cardiovascular disease includes a cytosine at position −444. In certain embodiments, the detecting is by a polymerase chain reaction. In some embodiments, the inflammation-mediated cardiovascular disease is atherosclerosis. In some embodiments, the human subject is a female human subject.

The invention also provides a device for use in detecting a predisposition to cardiovascular disease in a human subject, including a leukotriene C4 synthase (LTC4S) gene product affinity reagent immobilized on a surface of a solid support, and a reference known to be associated with a non-risk of development of an inflammation-mediated cardiovascular disease.

In some embodiments, the LTC4S gene product is a nucleic acid. In certain embodiments, the LTC4S gene product affinity reagent comprises a nucleic acid complementary to a LTC4S nucleic acid gene product. In some embodiments, the LTC4S gene product is a polypeptide. In certain embodiments, the LTC4S gene product affinity reagent comprises an anti-LTC4S polypeptide antibody or binding fragment thereof.

The invention also provides a kit for use in detecting a predisposition to an inflammation-mediated cardiovascular disease in a human subject, including reagents for assaying a sample for a leukotriene C4 synthase (LTC4S) gene product, and a reference known to be associated with a non-risk of development of an inflammation-mediated cardiovascular disease.

In some embodiments, the LTC4S gene product is a nucleic acid. In some embodiments, the LTC4S gene product is a polypeptide. In some embodiments, the reagents comprise at least one LTC4S gene product affinity reagent. In certain embodiments, the LTC4S gene product affinity reagent includes a forward primer and a reverse primer. In certain embodiments, the LTC4S gene product affinity reagent includes a nucleic acid complementary to a LTC4S nucleic acid gene product. In certain embodiments, the LTC4S gene product affinity reagent includes an anti-LTC4S polypeptide antibody or binding fragment thereof.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DEFINITIONS

Figure 1:
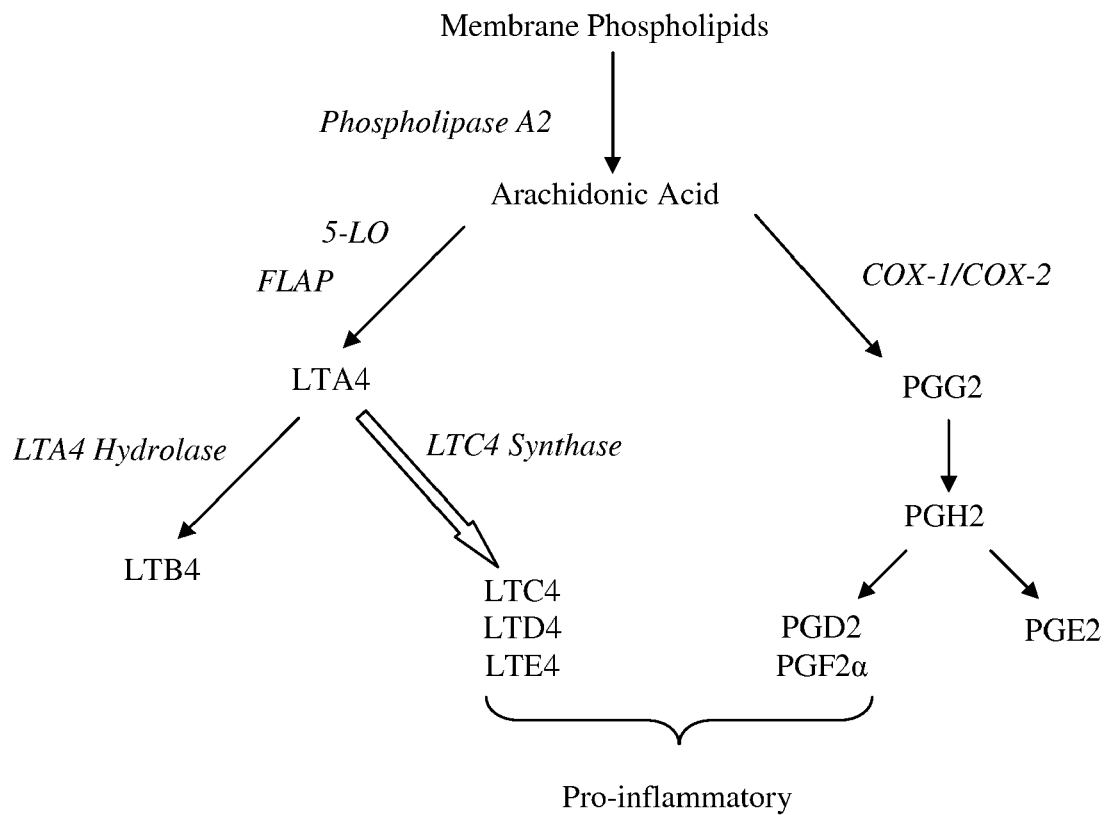
FIG. 1 is the biochemical pathway for arachidonic acid metabolism. Arachidonic acid is released from membrane phospholipids by the action of Phospholipase A2. Once generated, arachidonic acid may be metabolized by either the Lipoxygenase or the Cyclooxygenase pathways. Through the coordinated activity of 5-Lipoxygenase and 5-Lipoxygenase Activating Protein, arachidonic acid is converted to leukotriene A4. Leukotriene $C_4$ Synthase (open arrow), the rate limiting step along the cysteinyl-leukotriene pathway branch, converts leukotriene A4 to leukotriene $C_4$, which can subsequently be converted to the additional cysteinyl-leukotrienes, leukotriene D4 and leukotriene $E_4$. Leukotriene $C_4$, leukotriene $D_4$, and leukotriene $E_4$, each possess pro-inflammatory activities (abbreviations include: 5-LO=5-Lipoxygenase; FLAP=5-Lipoxygenase Activating Protein; COX=Cyclooxygenase; LT=leukotriene; PG=prostaglandin).

As used herein "leukotriene C4 synthase", "LTC4 synthase", or "LTC4S", refer to the enzyme of the arachidonic acid cascade that catalyzes the formation of LTC4 as shown in FIG. 1. The LTC4S gene includes a 4,465 nucleotide genomic sequence comprising 1,446 nucleotides of sequence 5' to the coding sequence, the 5 exons and intervening introns and 3' sequence extending 398 nucleotide beyond the poly A signal (Penrose et al., J. Biol. Chem., 271, 11356-11361 (1996)). The sequence of the protein can be found at GenBank Accession No. NP_665874, the sequence of the mRNA can be found at GenBank Accession No. NM_145867, the sequence of the gene can be found at GenBank Accession No. U62025, and the genomic sequence can be found at ref|NC_000005.8|NC_000005:179153592-179156119.

As used herein, "cardiovascular disease" refers to any manifestation of or predisposition to cardiovascular disease including, but not limited to, atherosclerosis, coronary artery disease and myocardial infarction. Included in predisposition is the manifestation of risks factors such as high serum cholesterol levels and low serum HDL levels.

As used herein, "inflammatory cardiovascular disease" or "inflammation-mediated cardiovascular disease" refers to any manifestation of or predisposition to cardiovascular disease that is associated with inflammation, such as atherosclerosis.

As used herein, "atherosclerosis" refers to a disease of the arterial blood vessels that results in hardening of the arteries caused by the formation of multiple atheromatous plaques within the arteries. Pathologically, the atheromatous plaque includes nodular accumulation of a soft, flaky, yellowish material at the center of large plaques, composed of macrophages nearest the lumen of the artery, sometimes with underlying areas of cholesterol crystals, and possibly also calcification at the outer base of older/more advanced lesions. The atheromatous plaques, though compensated for by artery enlargement, eventually lead to plaque ruptures and stenosis (i.e., narrowing) of the artery and, therefore, an insufficient blood supply to the organ it feeds. Alternatively, if the compensating artery enlargement process is excessive, then a net aneurysm results. The complications associated with atherosclerosis are chronic, slowly progressing and cumulative. Most commonly, the rupture of a soft plaque causes the formation of a blood clot (e.g., thrombus) that will rapidly slow or stop blood flow, e.g. 5 minutes, leading to death of the tissues fed by the artery. A common recognized scenario is coronary thrombosis of a coronary artery causing myocardial infarction (i.e., a heart attack). Another common scenario in advanced disease is claudication from insufficient blood supply to the legs, typically due to a combination of both stenosis and aneurysmal segments narrowed with clots. Kidney, intestinal and other arteries are also typically involved.

As used herein, "subject" or "patient" refers to any mammal, including humans, bovines, ovines, porcines, canines and felines, in need of treatment. In certain embodiments, the patient is a human, such as a female or male human subject. In general, the methods of the invention are applicable to adult patients.

As used herein, "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides in length.

As used herein, "polymorphic gene" refers to a gene having at least one polymorphic region.

As used herein, "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

As used herein, a "promoter region" refers to the portion of DNA of a gene that controls transcription of the DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated.

As used herein, "predisposition to develop a disease or disorder" means that a subject having a particular genotype and/or haplotype has a higher likelihood than one not having such a genotype and/or haplotype for developing a particular disease or disorder.

A "gene product" is a biopolymeric product that is expressed or produced by a gene. A gene product may be, for example, an unspliced RNA, an mRNA, a splice variant mRNA, a polypeptide, a post-translationally modified polypeptide, a splice variant polypeptide etc. Also encompassed by this term are biopolymeric products that are made using an RNA gene product as a template (i.e. cDNA of the RNA). A gene product may be made enzymatically, recombinantly, chemically, or within a cell to which the gene is native. In many embodiments, if the gene product is proteinaceous, it exhibits a biological activity. In many embodiments, if the gene product is a nucleic acid, it can be translated into a proteinaceous gene product that exhibits a biological activity.

The terms "polynucleotide" and "nucleic acid", used interchangeably herein, refer to polymeric forms of nucleotides of any length, either ribonucleotides or deoxynucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. These terms further include, but are not limited to, mRNA or cDNA that comprise intronic sequences (see, e.g., Niwa et al. (1999) Cell 99(7):691-702). The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. Peyrottes et al. (1996) Nucl. Acids Res. 24:1841-1848; Chaturvedi et al. (1996) Nucl. Acids Res. 24:2318-2323. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. The term "polynucleotide" also encompasses peptidic nucleic acids (Pooga et al Curr Cancer Drug Targets. (2001) 1:231-9).

Unless specifically indicated otherwise, there is no intended distinction in length between the terms "polynucleotide," "oligonucleotide," "nucleic acid" and "nucleic acid molecule" and these terms will be used interchangeably. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

Throughout the specification, abbreviations are used to refer to nucleotides (also referred to as bases), including abbreviations that refer to multiple nucleotides. As used herein, G=guanine, A=adenine, T=thymine, C=cytosine, and U=uracil. In addition, R=a purine nucleotide (A or G); Y=a pyrimidine nucleotide (A or T (U)); S=C or G; W=A or T (U); M=A or C; K=G or T (U); V=A, C or G; N=any nucleotide (A, T (U), C, or G); H=A or C or T (U); D=A or G or T (U); and B=C or G or T (U). Nucleotides can be referred to throughout using lower or upper case letters. It is also understood that nucleotides sequences provided for DNA in the specification also represent nucleotide sequences for RNA, where T is substituted by U.

The terms "deoxyribonucleic acid" and "DNA" as used herein mean a polymer composed of deoxyribonucleotides.

The terms "ribonucleic acid" and "RNA" as used herein refer to a polymer composed of ribonucleotides. Where sequences of a nucleic acid are provided using nucleotides of a DNA sequence, it is understood that such sequences encompass complementary DNA sequences and further also encompass RNA sequences based on the given DNA sequence or its complement, where uracil (U) replaces thymine (T) in the DNA sequence or its complement.

Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal concentration, and salt concentration. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

The terms "polypeptide" and "protein", interchangeably used herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

An "affinity reagent" of the subject invention has an analyte binding domain, moiety or component that has a high binding affinity for a target analyte. By high binding affinity is meant a binding affinity of at least about $10^{-4}$ M, usually at least about $10^{-6}$ M or higher, e.g., $10^{-9}$ M or higher. The affinity reagent may be any of a variety of different types of molecules, so long as it exhibits the requisite binding affinity for the target analyte, e.g., gene product, when present.

As such, the affinity reagent may be a small molecule or large molecule ligand. By small molecule ligand is meant a ligand ranging in size from about 50 to about 10,000 daltons, usually from about 50 to about 5,000 daltons and more usually from about 100 to about 1000 daltons. By large molecule is meant a ligand ranging in size from about 10,000 daltons or greater in molecular weight.

By "binds specifically" is meant high avidity and/or high affinity binding of an antibody to a specific antigen. Antibody binding to its epitope on this specific antigen is stronger than binding of the same antibody to any other epitope, particularly those which may be present in molecules in association with, or in the same sample, as the specific antigen of interest. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the polypeptide of interest, e.g., by use of appropriate controls.

As used herein, "treatment" or "treating" refers to inhibiting the progression of a disease or disorder, e.g., cardiovascular disease, including atherosclerosis, or delaying the onset of a disease or disorder, whether physically, e.g., stabilization of a discernible symptom, physiologically, e.g., stabilization of a physical parameter, or both. As used herein, the terms "treatment," "treating," and the like, refer to obtaining a desired pharmacologic and/or physiologic effect. The effect may be prophylactic in terms of completely or partially preventing a disease or condition, or a symptom thereof and/or may be therapeutic in terms of a partial or complete cure for a disease or disorder and/or adverse affect attributable to the disease or disorder. "Treatment," as used herein, covers any treatment of a disease or disorder in a mammal, such as a human, and includes: decreasing the risk of death due to the disease; preventing the disease or disorder from occurring in a subject which may be predisposed to the disease but has not yet been diagnosed as having it; inhibiting the disease or disorder, i.e., arresting its development (e.g., reducing the rate of disease progression); and relieving the disease, i.e., causing regression of the disease. Therapeutic benefits of the present invention include, but are not necessarily limited to, reduction of risk of onset or severity of disease or conditions associated with cardiovascular disease, e.g., atherosclerosis.

As used herein, a "therapeutically effective amount" refers to that amount of a compound sufficient to treat or manage a disease or disorder, e.g., cardiovascular disease, such as atherosclerosis. A therapeutically effective amount may refer to the amount of a compound that provides a therapeutic benefit in the treatment or management of a disease or disorder. Further, a therapeutically effective amount with respect to a compound means that amount of compound alone, or in combination with other therapies, that provides a therapeutic benefit in the treatment or management of a disease or disorder. The term can encompass an amount that improves overall therapy, reduces or avoids unwanted effects, or enhances the therapeutic efficacy of or synergies with another therapeutic agent.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, subcutaneous, intradermal, intratracheal and the like. In some embodiments the composition is suitable for administration by a transdermal route, using a penetration enhancer other than DMSO. In other embodiments, the pharmaceutical compositions are suitable for administration by a route other than transdermal administration.

As used herein, the phrase "pharmaceutically acceptable carrier" refers to a carrier medium that does not interfere with the effectiveness of the biological activity of the active ingredient. Said carrier medium is essentially chemically inert and nontoxic.

As used herein, the phrase "pharmaceutically acceptable" means approved by a regulatory agency of the Federal government or a state government, or listed in the U.S. Pharmacopeia or other generally recognized pharmacopeia for use in animals, and more particularly for use in humans.

As used herein, the term "carrier" refers to a diluent, adjuvant, excipient, or vehicle with which the therapeutic is administered. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The carrier, if desired, can also contain minor amounts of wetting or emulsifying agents, or pH buffering agents. These pharmaceutical compositions can take the form of solutions, suspensions, emulsion, tablets, pills, capsules, powders, sustained-release formulations and the like. The composition can be formulated as a suppository, with traditional binders and carriers such as triglycerides. Examples of suitable pharmaceutical carriers are described in *Remington's Pharmaceutical Sciences* by E. W. Martin. Examples of suitable pharmaceutical carriers are a variety of cationic polyamines and lipids, including, but not limited to N-(1(2,3-dioleyloxy)propyl)-N,N,N-trimethylammonium chloride (DOTMA) and diolesylphosphotidylethanolamine (DOPE). Liposomes are suitable carriers for gene therapy uses of the invention. Such pharmaceutical compositions should contain a therapeutically effective amount of the compound, together with a suitable amount of carrier so as to provide the form for proper administration to the subject. The formulation should suit the mode of administration.

As used herein, "pharmaceutically acceptable derivatives" of a compound includes salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

As used herein, the phrase "pharmaceutically acceptable salts" refers to salts prepared from pharmaceutically acceptable, essentially nontoxic, acids and bases, including inorganic and organic acids and bases. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

As used herein, an "immediate release" formulation of a compound refers to a drug composition or mixture of drug compositions in which there is no carrier that regulates the bioavailability of the drug's active ingredient(s) to tissues at the site of drug administration in the patient's body. It will be understood that any component of the formulation that limits or impairs access of the drug's active ingredient(s) to tissues at the site of drug administration in the patient's body is a carrier that regulates the bioavailability of the active ingredient(s) so affected for purposes of the foregoing definition.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same or different routes, and in the same or different dosage form type.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Before the present invention described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods and compositions for detecting a predisposition to an inflammation-mediated cardiovascular disease in a human subject by detecting a level of leukotriene C4 synthase (LTC4S) gene product in a sample from a human subject indicative of a predisposition to an inflammation-mediated cardiovascular disease or detecting the presence or absence of an allele of LTC4S indicative of a predisposition to an inflammation-mediated cardiovascular disease. In addition, the present invention also provides kits for practicing the methods.

The inventors have found an association between certain alleles of the LTC4 synthase gene and a predisposition to development of an inflammation-mediated cardiovascular disease, such as atherosclerosis. In particular, the inventors have discovered that individuals carrying certain single nucleotide polymorphisms in the LTC4 synthase gene that result in an increase in expression of the encoded protein have a predisposition to developing an inflammation-mediated cardiovascular disease, such as atherosclerosis.

Figure 2:
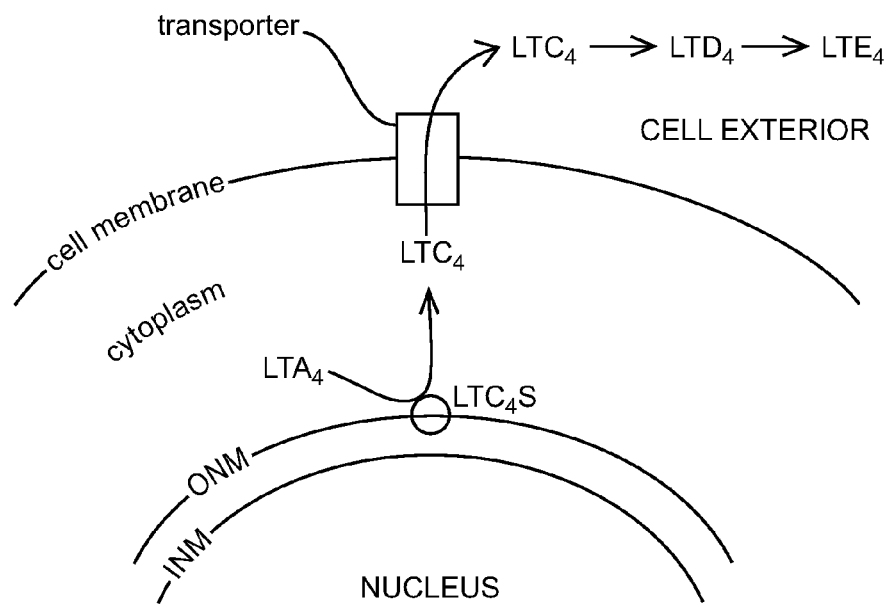
FIG. 2 is a schematic showing synthesis of cysteinyl-leukotriens (e.g., LTC4, LTD4, and LTE4) and interaction of the cysteinyl-leukotriens with target cell receptors. Panel A shows LTC4S, located on the outer nuclear membrane (ONM) which catalyzes the synthesis of leukotriene C4 (LTC4) from leukotriene A4 (LTA4) and the subsequent release of LTC4 from the cell. Leukotriene D4 (LTD4) and leukotriene E4 (LTE4) are synthesized sequentially from LTC4. Panel B shows interaction of the inflammatory cysteinyl-leukotrienes with either of two cysteinyl-leukotriene receptors (CYSLTR1 and CYSLTR2) located on the cytoplasmic membrane of target cells. For example, CYSLTR1 is expressed on eosinophils and leukocytes, and CYSLTR2 is expressed on macrophages and some cardiac cells. Binding of the inflammatory cysteinyl-leukotrienes is followed by receptor internalization and migration to the cell's nucleus where the cascade of inflammatory events, such as synthesis and release of inflammatory cytokines, resulting in the stimulation and recruitment of additional inflammatory cells, is amplified. (Receptor internalization and subsequent steps are not depicted).
Figure 2:
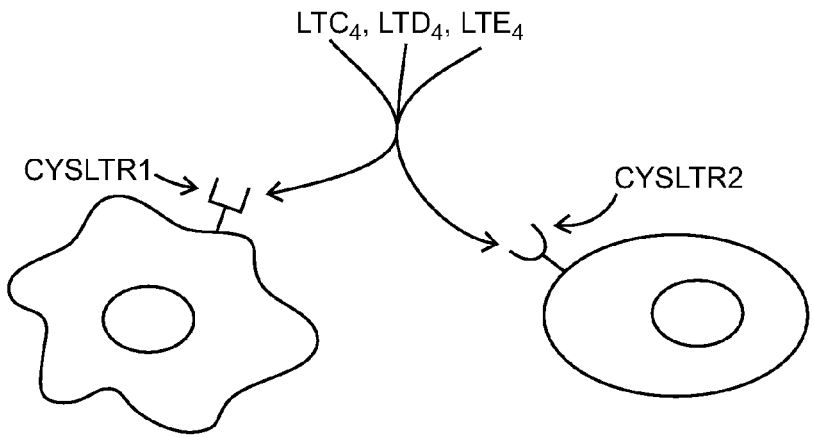

LTC4S in involved in the conversion of arachidonic acid to cysteinyl-leukotrienes (cys-LTs), which are mediators of the inflammatory response (FIG. 2). In this pathway, arachidonic acid is first converted to the epoxide intermediate leukotriene A4 by the coordinated activity of 5-Lipoxygenase and 5-Lipoxygenase activating protein (FIG. 1 and FIG. 2, Panel A). Additional leukotrienes are subsequently generated through the specific conjugation of leukotriene A4 with glutathione by LTC4S, leading to the formation of leukotriene $C_4$ (FIG. 2, Panel A). Sequential removal of the glutamic acid and glycine residues from the glutathione moiety of leukotriene $C_4$ leads to the formation of leukotriene $D_4$ and leukotriene $E_4$, respectively (FIG. 2, Panel A). Leukotriene $C_4$, $-D_4$ and $-E_4$ which together compose the cys-LTs, are potent mediators of inflammation by their abilities to stimulate sustained smooth muscle contraction, mucus hypersecretion airway edema and eosinophil recruitment (FIG. 2, Panel B).

The inventors have found that promoter region sequence alterations (e.g., sequence alteration at position −444 A>C) resulting in upregulation of LTC4S mRNA expression result in a subsequent increase in the levels of the inflammatory molecules $LTC_4$, $LTD_4$ and $LTE_4$. As such, the methods are based on detection of an increase in LTC4S gene product in a subject, such as mRNA or protein, as being indicative of a predisposition to develop an inflammation-mediated cardiovascular disease. Likewise, detection of the presence of a predisposing LTC4S allele is also indicative of a predisposition to development of an inflammation-mediated cardiovascular disease.

The following description provides guidance for carrying out the methods of the invention.

Methods

As summarized above, the present invention provides methods for determining whether a human subject has a predisposition for developing an inflammation-mediated cardiovascular disease, such as atherosclerosis. In one aspect, the methods provide for detecting the level of a LTC4S gene product in a sample from a human subject as compared to a reference value known to be not associated with a predisposition for development of an inflammation mediated disease. In such embodiments, detection of an increased level of the LTC4S gene product as compared to the reference value indicates that the human subject has a predisposition for developing an inflammation-mediated cardiovascular disease. In another aspect, the methods provide for detecting a predisposition to an inflammation-mediated cardiovascular disease in a human subject, by detecting the presence or absence of a predisposing allele of a leukotriene C4 synthase (LTC4S), wherein the presence of the allele indicates the human subject has a predisposition to an inflammation-mediated cardiovascular disease.

Detection of a LTC4S Gene Product

In determining whether a human subject at least has a predisposition for the development of an inflammation-mediated cardiovascular disease, a sample from the human subject is assayed to determine the level of LTC4S gene product present in the sample. By "leukotriene C4 synthase", "LTC4 synthase", or "LTC4S", is meant the enzyme of the arachidonic acid cascade that catalyzes the formation of LTC4 as shown in FIG. 1. The LTC4S gene includes a 4,465 nucleotide genomic sequence comprising 1,446 nucleotides of sequence 5' to the coding sequence, the 5 exons and intervening introns and 3' sequence extending 398 nucleotide beyond the poly A signal (Penrose et al., J. Biol. Chem., 271, 11356-11361 (1996)).

A gene product may be, for example, an unspliced RNA, an mRNA, a splice variant mRNA, a polypeptide, a post-translationally modified polypeptide, a splice variant polypeptide etc. The sequence of the LTC4S protein can be found at GenBank Accession No. NP_665874, the sequence of the LTC4S mRNA can be found at GenBank Accession No. NM_145867, the sequence of the LTC4S gene can be found at GenBank Accession No. U62025, and the genomic sequence can be found at ref|NC_000005.8|NC_000005: 179153592-179156119. As such, in certain embodiments the LTC4S gene product of interest for which a given sample is assayed is the LTC4S polypeptide or the LTC4S mRNA.

As summarized above, in practicing the subject methods a sample from a subject is assayed for the level of a LTC4S gene product. The sample that is assayed is a sample that is, or is derived from, any initial source that contains a LTC4S gene product. In certain embodiments, a suitable sample will be one that is suitable source of eosinophils. Accordingly, a suitable sample source will be derived from fluids into which the LTC4S gene product is present or has been released therein. Sample sources of interest include, but are not limited to, an artery scarping, a blood clot, and many different bodily fluids, e.g., serum, plasma, blood, urine, mucus, and lymph, particularly blood or blood products and urine. Sample sources of particular interest include blood samples, e.g., whole blood, serum or plasma, and urine. A sample volume of blood, serum, or urine between about 2 µl to about 2,000 µl is sufficient for determining the level of a LTC4S gene product. Generally, the sample volume will range from about 10 µl to about 1,750 µl, from about 20 µl to about 1,500 µl, from about 40 µl to about 1,250 µl, from about 60 µl to about 1,000 µl, from about 100 µl to about 900 µl, from about 200 µl to about 800 µl, from about 400 µl to about 600 µl.

Appropriate control samples for the assay include blood, serum, or urine collected from human subjects who are known to not have a predisposition for development of an inflammation-mediated cardiovascular disease or do not have a predisposing allele of the LTC4S gene (i.e., a negative control), or samples which contain a known, predetermined amount of a LTC4S gene product (i.e., a positive control).

In many embodiments, a suitable initial source for the human sample is a blood sample. As such, the sample employed in the subject assays is generally a blood-derived sample. The blood derived sample may be derived from whole blood or a fraction thereof, e.g., serum, plasma, etc., where in some embodiments the sample is derived from blood allowed to clot and the serum separated and collected to be used to assay.

In embodiments in which the sample is a serum or serum derived sample, the sample is generally a fluid sample. Any convenient methodology for producing a fluid serum sample may be employed. In many embodiments, the method employs drawing venous blood by skin puncture (e.g., finger stick, venipuncture) into a clotting or serum separator tube, allowing the blood to clot, and centrifuging the serum away from the clotted blood. The serum is then collected and stored until assayed. Once the patient derived sample is obtained, the sample is assayed to determine the level of a LTC4S gene product.

The subject sample may be treated in a variety of ways so as to enhance detection of a LTC4S gene product. For example, where the sample is blood, the red blood cells may be removed from the sample (e.g., by centrifugation) prior to assaying. Such a treatment may serve to reduce the non-specific background levels of detecting the level of LTC4S gene product using an affinity reagent. Detection of a LTC4S gene product may also be enhanced by concentrating the sample using procedures well known in the art (e.g. acid precipitation, alcohol precipitation, salt precipitation, hydrophobic precipitation, filtration (using a filter which is capable of retaining molecules greater than 30 kD, e.g. Centrim 30™), affinity purification). In some embodiments, the pH of the test and control samples will be adjusted to, and maintained at, a pH which approximates neutrality (i.e. pH 6.5-8.0). Such a pH adjustment will prevent LTC4S gene product complex formation, thereby providing a more accurate quantitation of the level of LTC4S gene product in the sample.

The sample may be assayed to determine the presence and/or amount (i.e., level) of a LTC4S gene product, such as mRNA or polypeptide, using any convenient methodology. In some embodiments, where the LTC4S gene product is a polypeptide, the level of the LTC4S gene product is determined by using a LTC4S gene product affinity reagent, such as an anti-LTC4S antibody or binding fragment.

As reviewed above, the affinity reagent (i.e. LTC4S gene product binding reagent) is a molecule that has a high binding affinity for a LTC4S gene product, such as a LTC4S polypeptide. By high binding affinity is meant a binding affinity of at least about $10^{-4}$ M, usually at least about $10^{-6}$ M or higher, e.g., $10^{-9}$ M or higher. The affinity reagent may be any of a variety of different types of molecules, so long as it exhibits the requisite binding affinity for a LTC4S gene product, such as a LTC4S polypeptide.

As such, the affinity reagent may be a small molecule or large molecule ligand. By small molecule ligand is meant a ligand ranging in size from about 50 to about 10,000 daltons, usually from about 50 to about 5,000 daltons and more usually from about 100 to about 1000 daltons. By large molecule ligand is meant a ligand ranging in size from about 10,000 daltons or greater in molecular weight.

The small molecule may be any molecule, as well as binding portion or fragment thereof, that is capable of binding with the requisite affinity to the target protein. Generally, the small molecule is a small organic molecule that is capable of binding to the target analyte of interest. The small molecule will include one or more functional groups necessary for structural interaction with a LTC4S gene product, such as a LTC4S polypeptide, e.g., groups necessary for hydrophobic, hydrophilic, electrostatic or even covalent interactions. Suitable molecules will include functional groups necessary for structural interaction with a LTC4S gene product, such as hydrogen bonding, hydrophobic-hydrophobic interactions, electrostatic interactions, etc., and will typically include at least an amine, amide, sulfhydryl, carbonyl, hydroxyl or carboxyl group, preferably at least two of the functional chemical groups.

Of particular interest are anti-LTC4S polypeptide antibodies, as well as binding fragments and mimetics thereof. As such, the affinity reagent may be either a monoclonal and polyclonal antibody. In yet other embodiments, the affinity reagent is an antibody binding fragment or mimetic, where these fragments and mimetics have the requisite binding affinity for a LTC4S polypeptide. For example, antibody fragments, such as Fv, F(ab)$_2$ and Fab may be prepared by cleavage of the intact protein, e.g. by protease or chemical cleavage. Also of interest are recombinantly produced antibody fragments, such as single chain antibodies or scFvs, where such recombinantly produced antibody fragments retain the binding characteristics of the above antibodies. Such recombinantly produced antibody fragments generally include at least the VH and VL domains of the subject antibodies, so as to retain the binding characteristics of the subject antibodies. These recombinantly produced antibody fragments or mimetics of the subject invention may be readily prepared using any convenient methodology, such as the methodology disclosed in U.S. Pat. Nos. 5,851,829 and 5,965,371; the disclosures of which are herein incorporated by reference.

The above described antibodies, fragments and mimetics thereof may be obtained from commercial sources and/or prepared using any convenient technology, where methods of producing polyclonal antibodies, monoclonal antibodies, fragments and mimetics thereof, including recombinant derivatives thereof, are known to those of the skill in the art.

Also suitable for use as an affinity reagent are polynucleic acid aptamers. Polynucleic acid aptamers may be RNA oligonucleotides which may act to selectively bind proteins, much in the same manner as a receptor or antibody (Conrad et al., Methods Enzymol. (1996), 267 (Combinatorial Chemistry), 336-367).

Any convenient assay protocol may be employed. Suitable assays that may be employed include antibody-based immunoassays, e.g. an ELISA. Antibody based assays require the use of antibodies, or fragments and mimetics thereof, specific for a LTC4S polypeptide. Of interest are direct assays, i.e., those which employ antibodies, or fragments and mimetics thereof, specific for a LTC4S polypeptide.

Antibodies that specifically bind to a LTC4S polypeptide can be prepared using a variety of convenient methods known to those of skill in the art. See Guide to Protein Purification, supra, as well as Antibodies, A Laboratory Manual (Harlow & Lane eds. Cold Spring Harbor Press, 1988). The antibodies may be polyclonal or monoclonal antibodies depending on the nature of the intended use, as long as they are specific for a LTC4S polypeptide.

The antibodies, fragments or derivatives thereof may also be labeled in order to facilitate detection. A variety of protein labeling schemes are known in the art and may be employed, the particular scheme and label chosen being the one most convenient for the intended use of the antibody, e.g. immunoassay. Examples of labels include labels that permit both the direct and indirect measurement of the presence of the antibody. Examples of labels that permit direct measurement of the antibody include radiolabels, such as $^3$H or $^{125}$I, fluorescers, dyes, beads, chemilumninescers, colloidal particles, and the like. Examples of labels which permit indirect measurement of the presence of the antibody include enzymes where a substrate may provide for a colored or fluorescent product. For example, the antibodies may be labeled with a covalently bound enzyme capable of providing a detectable product signal after addition of suitable substrate. Instead of covalently binding the enzyme to the antibody, the antibody may be modified to comprise a first member of specific binding pair which specifically binds with a second member of the specific binding pair that is conjugated to the enzyme, e.g. the antibody may be covalently bound to biotin and the enzyme conjugate to streptavidin. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

The assay of the subject invention may be performed in solution or may use a solid (insoluble) support (e.g. polystyrene, nitrocellulose, or beads), using any standard methods (e.g., as described in Current Protocols in Immunology, Coligan et al., ed.; John Wiley & Sons, New York, 1992). Typical methods include ELISAs (enzyme-linked immunosorbent assays), IRMAs (immunoradiometric assays), and RIAs (radioimmunoassays). Where the assay is performed in solution, the test and control samples are each incubated with a LTC4S polypeptide affinity reagent for a time period sufficient to allow formation of analyte and affinity reagent complexes, preferably between about 0.1 hrs up to 24 hrs, or more. As previously noted, the affinity reagent may include a detectable label (e.g. radionuclide, fluorescer, or enzyme). The sample is then treated to separate the analyte and affinity reagent complexes from excess, unreacted affinity reagent (e.g. by addition of anti-affinity reagent (e.g., anti-immunoglobulin antiserum) followed by centrifugation (e.g., 1000 xg for 7 min) to precipitate the analyte and affinity reagent complexes, or by binding to an affinity surface such as a second, unlabelled LTC4S polypeptide affinity reagent (e.g., antibody) fixed to a solid substrate such as Sepharose or a plastic well). Detection of affinity reagent bound to a LTC4S polypeptide may be achieved in a variety of ways well known in the art. If necessary, a substrate for the detectable label may be added to the sample.

Where the assay uses a solid support, the support will have an affinity reagent capable of specifically binding a LTC4S polypeptide, where the affinity reagent is bound to the support surface. The affinity reagent facilitates the stable, wash-resistant binding of a LTC4S polypeptide present in the sample to the solid support. The insoluble supports may be any compositions to which affinity reagents, such as antibodies or fragments and mimetics thereof can be bound, which is readily separated from soluble material, and which is otherwise compatible with the overall method of measuring a LTC4S polypeptide in the sample. The surface of such supports may be solid or porous and of any convenient shape. Examples of suitable insoluble supports to which the affinity reagent is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples. Suitable affinity reagents include antibodies, or fragments and mimetics thereof, which specifically bind a LTC4S polypeptide, or anti-idiotype antibodies, or fragments and mimetics thereof, which specifically bind to the anti-LTC4S polypeptide-antibody.

Methods for binding affinity reagents (e.g., antibodies, or fragments and mimetics thereof) to solid supports are well known in the art. After binding of the affinity reagent to the support, the support may be treated with a blocking agent, which binds to the support in areas not occupied by the affinity reagent. Suitable blocking agents include non-interfering proteins such as bovine serum albumin, casein, gelatin, and the like. Alternatively, several detergents at non-interfering concentrations, such as Tween, NP40, TX100, and the like may be used. Such blocking treatment reduces nonspecific binding.

In certain embodiments, a series of standards, containing known concentrations of LTC4S polypeptide may be assayed in parallel with the samples or aliquots thereof to serve as controls. Generally from about 0.001 to 1 ml of sample, diluted or otherwise, is sufficient, usually about 0.01 ml sufficing. Furthermore, in certain embodiments, each sample and standard will be added to multiple wells so that mean values can be obtained for each.

The test and control samples are each incubated with the solid support for a time sufficient for binding of a LTC4S polypeptide to the affinity reagent. The incubation time should be sufficient for a LTC4S polypeptide to bind the insoluble first affinity reagent. Generally, from about 0.1 to 3 hr is sufficient, usually 1 hr sufficing. After incubation, the reacted samples may be washed to remove unbound or non-specifically bound material. Generally, a dilute non-ionic detergent medium at an appropriate pH, generally 7-8, is used as a wash medium. An isotonic buffer, such as phosphate-buffered saline, may be employed in the washing step. From one to six washes may be employed, with sufficient volume to thoroughly wash non-specifically bound proteins present in the sample. Preferably, the washing step will not cause dissociation of LTC4S polypeptide and affinity reagent complexes.

A second affinity reagent which specifically binds a LTC4S polypeptide is then incubated with the LTC4S polypeptide-affinity reagent complexes. In some embodiments the second affinity reagent is an anti-LTC4S polypeptide antibody, or fragment and mimetic thereof, where the second affinity reagent preferably binds to an epitope different from the epitope bound by the first affinity reagent. The second affinity reagent (e.g., antibody) used to detect a LTC4S polypeptide bound to the support may be detectably labeled to facilitate direct, or indirect detection of LTC4S polypeptide-first affinity reagent-second affinity reagent complexes.

Examples of labels which permit direct measurement of immunocomplexes include radiolabels, such as $^3$H or $^{125}$I, fluorescers, dyes, beads, chemilumninescers, colloidal particles, and the like. Examples of labels which permit indirect measurement of binding include enzymes where the substrate may provide for a colored or fluorescent product. In some embodiment, the second affinity reagent (e.g., antibody or fragment and mimetic thereof) is labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such affinity reagent-enzyme conjugates are readily produced by techniques known to those skilled in the art.

Alternatively, a third detectably labeled affinity reagent (e.g., antibody, or fragment and mimetic thereof) which specifically binds the second affinity reagent may be used to detect the LTC4S polypeptide-first affinity reagent-second affinity reagent complexes. Examples of third affinity reagent/second affinity reagent-specific molecule pairs include antibody/anti-antibody and avidin (or streptavidin)/biotin. Since the resultant signal is thus amplified, this technique may be advantageous where only a small amount of a LTC4S polypeptide is present in the sample. An example is the use of a labeled antibody specific to the second antibody. The volume, composition and concentration of the third affinity reagent solution provides for measurable binding to the LTC4S polypeptide already bound to the second affinity reagent. Generally, the same volume as that of the sample is used: from about 0.001 to 1 ml is sufficient, usually about 0.1 ml sufficing. The concentration will generally be sufficient to saturate the LTC4S polypeptide potentially bound to second reagent.

In such assays, the concentration of the second affinity reagent will generally be about 0.1 to 50 µg/ml, preferably about 1 µg/ml. The solution containing the second antibody is generally buffered in the range of about pH 6.5-9.5. The incubation time should be sufficient for the second affinity reagent to bind available molecules. Generally, from about 0.1 to 3 hr is sufficient, usually 1 hr sufficing. After the second affinity reagent has bound, the insoluble support is generally again washed free of non-specifically bound second receptor, essentially as described for prior washes. After non-specifically bound material has been cleared, the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490-495 nm is conveniently measured with a spectrophotometer.

Alternatively, a LTC4S gene product, such as a LTC4S polypeptide, may be detected by using a competitive binding assay. The test and control samples are incubated with the anti-LTC4S polypeptide affinity reagent as described above (e.g., anti-LTC4S polypeptide antibody or binding fragment), to allow for formation of LTC4S polypeptide-affinity reagent complexes. The affinity reagent may be fixed to a solid surface or in solution. After washing to remove unbound material from the precipitated LTC4S polypeptide-affinity reagent complexes or from the solid support (if any) to which the antibody is fixed, the samples are then incubated with a standard amount of detectably labeled LTC4S polypeptide or a detectably labeled fragment of LTC4S polypeptide which retains the ability to compete with a native LTC4S polypeptide for binding sites on the anti-LTC4S polypeptide analyte binding reagent. Binding is detected by standard means: e.g., by measuring the amount of label associated with (a) the solid support (if any), or (b) the precipitated analyte/binding agent complexes. A lower level of binding of the detectably labeled LTC4S polypeptide in the test sample than in the negative control indicates the presence of an elevated level of LTC4S polypeptide in the test sample.

Alternatively, the binding of the second LTC4S polypeptide used in the competitive binding assay (i.e. the LTC4S polypeptide introduced into the test sample after incubation of the test sample with the anti-LTC4S polypeptide analyte affinity reagent), may be measured by means of an epitope present on the second LTC4S polypeptide which is absent in a LTC4S polypeptide derived from a sample of bodily fluid. For example, the second LTC4S polypeptide may be a recombinant fusion protein which retains the ability to bind competitively to the affinity reagent used in the assay. Binding of the LTC4S polypeptide fusion protein to the anti-LTC4S polypeptide affinity reagent may then be detected by incubating the sample with a detectably labeled second affinity reagent which specifically binds the fusion protein and does not bind the LTC4S polypeptide from the sample. An example of a recombinant LTC4S polypeptide fusion protein is one that containing an N-terminal extension of amino acids, which recombinant LTC4S polypeptide fusion protein may be used in such a detection method, since affinity reagents which specifically bind to the N-terminal amino acid extension of the recombinant molecule would not be expected to bind to a LTC4S polypeptide analyte present in a sample.

As summarized above, the subject methods are used to determine at least the presence and often the amount (i.e., level) of a LTC4S gene product present in sample from a human subject to determine whether the human subject has a predisposition for developing an inflammation-mediated cardiovascular disease. Specifically, in some embodiments, determining the level of a LTC4S gene product in a sample according to the subject methods typically involves comparing the detected signal obtained from the subject methods to a table or other source of predetermined values or reference values (collectively referred to herein as a reference) known to be not associated with a risk (i.e., not at risk) of development of an inflammation-mediated cardiovascular disease. For example, a table of values may be consulted in this step, where the table comprises representative values for a LTC4S gene product as found in patients known to be not at risk or predisposed to developing an inflammation-mediated cardiovascular disease, such as atherosclerosis, involving abnormal levels of a LTC4S gene product.

The values may be presented in numerical form, in picture form (e.g. as bands on a gel), and the like. By comparing the observed values with these reference values, e.g. by comparing a pattern of expression of a LTC4S gene product in the sample to a reference pattern or picture, characterization of the disease activity, e.g. confirmation of diagnosis, determination of disease state, etc., is readily made.

In other embodiments, determining the level of a LTC4S gene product in a sample according to the subject methods involves comparing the level of anti-LTC4S gene product affinity reagent binding in the test sample to the level of anti-LTC4S gene product affinity reagent binding in the negative and/or positive control samples. In such embodiments the level of affinity reagent binding in the test sample is compared to a range of negative and positive control sample, in which the positive control samples have a range of predetermined quantities of LTC4S gene product present, where certain samples have levels of LTC4S gene product known to be not at risk or predisposed to developing a inflammation-mediated cardiovascular disease, and other samples have levels of LTC4S gene product known to be at risk or predisposed to developing a inflammation-mediated cardiovascular disease, and the negative control samples do not have any LTC4S gene product present.

Detection of a Predisposing Allele of LTC4S

The present invention also provides a method of detecting a predisposition to an inflammation-mediated cardiovascular disease in a human subject by detecting the presence or absence of an allele of a leukotriene C4 synthase (LTC4S) indicative of a predisposition to an inflammation-mediated cardiovascular disease, wherein the presence of the allele indicates the human subject has a predisposition to an inflammation-mediated cardiovascular disease.

By "predisposing mutation in LTC4S" or "predisposing allele of LTC4S" is meant an allele of LTC4S that provides an increase in expression of the LTC4S polypeptide as compared to a reference level known to be not associated with a predisposition for developing inflammation-mediated cardiovascular disease, such as atherosclerosis. Exemplary mutations or alleles of LTC4S that provide for in increased or elevated level of the LTC4S polypeptide are those mutations present in the promoter region of the LTC4S gene, such as the 5' untranslated region of the gene, that result in an increase in expression of the gene or decrease in repression of the gene. In other words, the mutation results in an increase in LTC4S mRNA and thereby an increase in LTC4S polypeptide in the human subject. Exemplary predisposing alleles of the LTC4S gene are described in U.S. Pat. No. 6,316,196, the disclosure of which is incorporated herein by reference in its entirety. In some embodiments, the predisposing allele of LTC4S is an allele that includes a substitution of position −444, where a cytosine is present instead of an adenine.

A number of methods are suitable for use in determining the presence of a predisposing mutation of LTC4S in an individual. Genomic DNA is isolated from the individual or individuals that are to be tested. DNA can be isolated from any nucleated cellular source such as blood, hair shafts, saliva, mucous, biopsy, feces, etc. Methods using PCR amplification can be performed on the DNA from a single cell, although it is convenient to use at least about $10^5$ cells. Where large amounts of DNA are available, the genomic DNA is used directly. Alternatively, the region of interest is cloned into a suitable vector and grown in sufficient quantity for analysis, or amplified by conventional techniques. Of particular interest is the use of the polymerase chain reaction (PCR) to amplify the DNA that lies between two specific primers. The use of the polymerase chain reaction is described in Saiki et al. (1985) *Science* 239:487, and a review of current techniques may be found in McPherson et al. (2000) PCR (Basics: From Background to Bench) Springer Verlag; ISBN: 0387916008. A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4', 7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Primer pairs are selected from the LTC4S genomic sequence using conventional criteria for selection. The primers in a pair will hybridize to opposite strands, and will collectively flank the region of interest. The primers will hybridize to the complementary sequence under stringent conditions, and will generally be at least about 16 nt in length, and may be 20, 25 or 30 nucleotides in length. The primers will be selected to amplify the specific region of the LTC4S gene suspected of containing the predisposing mutation. Typically the length of the amplified fragment will be selected so as to allow discrimination between alleles. Multiplex amplification may be performed in which several sets of primers are combined in the same reaction tube. Each primer may be conjugated to a different label.

The primers are used to amplify the region of genomic DNA that contains the single nucleotide polymorphism. Conveniently, a detectable label will be included in the amplification reaction, as previously described. Multiplex amplification may be performed in which several sets of primers are combined in the same reaction tube. This is particularly advantageous when limited amounts of sample DNA are available for analysis. Conveniently, each of the sets of primers is labeled with a different fluorochrome.

After amplification, the products may be size fractionated. Fractionation may be performed by gel electrophoresis, particularly denaturing acrylamide or agarose gels. A convenient system uses denaturing polyacrylamide gels in combination with an automated DNA sequencer, see Hunkapillar et al. (1991) Science 254:59-74. The automated sequencer is particularly useful with multiplex amplification or pooled products of separate PCR reactions. Capillary electrophoresis may also be used for fractionation. A review of capillary electrophoresis may be found in Landers, et al. (1993) Bio-Techniques 14:98-111. The size of the amplification product is proportional to the number of repeats (n) that are present at the locus specified by the primers. The size will be polymorphic in the population, and is therefore an allelic marker for that locus.

The amplified or cloned fragment may be sequenced by dideoxy or other methods, and the length of the amplified region, or the sequence of bases, is compared to the normal LTC4S sequence. Alternatively, where the predisposing mutation creates or destroys a recognition site for a restriction endonuclease, the fragment is digested with that endonuclease, and the products size fractionated to determine whether the fragment was digested. Fractionation is performed by gel electrophoresis, particularly acrylamide or agarose gels. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices is used to detect conformational changes created by DNA sequence variation as alterations in electrophoretic mobility. The hybridization pattern of a control and variant sequence to an array of oligonucleotide probes immobilized on a microarray, may also be used as a means of detecting the presence of variant sequences.

Many current methods for the detection of allelic variation are reviewed by Nollau et al., Clin. Chem. 43, 1114-1120, 1997; and in standard textbooks, for example "Laboratory Protocols for Mutation Detection", Ed. by U. Landegren, Oxford University Press, 1996 and "PCR", 2.sup.nd Edition by Newton & Graham, BIOS Scientific Publishers Limited, 1997.

The presence of a predisposing mutation is indicative that an individual is at increased risk of developing atherosclerosis. The diagnosis of a disease predisposition allows the affected individual to seek early treatment of potential lesions, and to avoid activities that increase risk for cardiovascular disease.

Devices

Also provided are devices that find use in practicing the subject methods, as described above. Devices for practicing the subject methods at least include reagents for assaying a sample derived from a human subject for a LTC4S gene product, where such devices may include: LTC4S gene product affinity reagents, such as an antibody, or fragment or mimetic thereof, immobilized on the surface of a solid support.

Additional items that are required or desired in the methods to be practiced with the devices may be present, which additional items include, but are not limited to: means for obtaining the patient sample, e.g. a syringe; one or more reagents necessary for preparation of the patient derived sample, lysing buffer, protease inhibitor, and the like; instructions for carrying out the subject methods using the subject devices; one or more reagents from an additional biochemical assay which is used to detect the level of and/or characterize the predisposition of the subject to developing a inflammation-mediated cardiovascular disease. In certain embodiments, the devices are provided with a reference, as described above, known to be associated with a non-risk of development of an inflammation-mediated cardiovascular disease.

A number of such devices are known in the art. In one non-limiting example, the apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it the first affinity reagent, and second labeled affinity reagent combined with the assayed sample and the sandwich assay performed as above.

In another non-limiting example the device is a dipstick, to the surface of which is bound an affinity reagent, such an antibody, or fragment or mimetic thereof, which specifically binds a LTC4S gene product. In such an exemplary device, the dipstick is inserted directly into a test sample (e.g., blood, serum, or urine) derived from a human subject for a period of time sufficient to permit binding of a LTC4S gene product to the affinity reagent bound to the dipstick. The dipstick may be then withdrawn and, if necessary, washed to remove nonspecifically bound material. The dipstick is then inserted into a container containing a detectably labeled second affinity reagent, such an antibody, or fragment or mimetic thereof, which specifically binds a LTC4S gene product. After incubation for a time sufficient for binding of the second antibody to the LTC4S gene product-affinity reagent complexes, the dipstick may be washed and binding of the second affinity reagent detected by standard means. Where necessary for detection of the second antibody, the dipstick may be inserted into a second container containing a reagent which activates the detectable label on the second antibody.

Kits

Also provided are kits that find use in practicing the subject methods, as described above. The kits for practicing the subject methods at least include reagents for assaying a sample derived from a human subject for a LTC4S gene product, where such kits may include: LTC4S gene product affinity reagents, such as an anti-LTC4S polypeptide antibody, or fragment or mimetic thereof, and/or immunoassay devices comprising the same members of a signal producing system, such as antibodies, enzyme substrates, and the like; various buffers for use in carrying out the subject detection assays; a reference for determining the amount of a LTC4S gene product in a sample; and the like.

In certain embodiments, the kits further include at least an information storage and presentation medium that contains reference data with which assay results may be compared in order to determine whether the subject has a predisposition for developing an inflammation-mediated cardiovascular disease, i.e., reference data that that positively or negatively correlate (e.g., at risk or not at risk) to a predisposition for developing an inflammation-mediated cardiovascular disease. The information storage and presentation medium may be in any convenient form, such as a printed information on a package insert, an electronic file present on an electronic storage medium, e.g. a magnetic disk, CD-ROM, and the like.

In yet other embodiments, the kits may include alternative means for obtaining reference data, e.g. a website for obtaining the reference data "on-line."

The kits may further include means for obtaining the patient sample, e.g. a syringe. The subject kits further typically include instructions for carrying out the subject methods, where these instructions may be present on a package insert and/or the packaging of the kit. Finally, the kit may further include one or more reagents from an additional biochemical assay which is used to detect the presence of and/or characterize the predisposition for developing an inflammation-mediated cardiovascular disease involving abnormal levels a LTC4S gene product or presence of a predisposing allele of the LTC4S gene.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The kit components may be present in separate containers, or one or more of the components may be present in the same container, where the containers may be storage containers and/or containers that are employed during the assay for which the kit is designed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods and materials are used in the examples below.

Study Population

Between 1971 and 1981, 11,377 school children 8 to 18 years of age from Muscatine, Iowa underwent 26,919 total examinations in six biennial school surveys. Between 1981 and 1991, 2,547 of the school survey participants (67% of those eligible) who were then 20 to 37 years of age were examined (anthropometric, blood pressure, lipid measurements and health history questionnaires) one or two times during the Young Adult Follow-up phase of The Muscatine Study. Between 1992 and 1996, a representative subset of the Young Adult Follow-up participants was invited to undergo a clinic examination and electron beam computed tomographic (EBCT) scanning for the measurement of coronary artery calcium (CAC). More than 95% of those invited became members of the Longitudinal Adult Cohort (n=866, 29 to 43 years of age; ethnicity=98% Caucasian). Childhood risk factor levels (adjusted for age, gender, and survey year) of the 866 cohort members did not differ significantly from the entire group of childhood participants with respect to height, weight, blood pressures, triceps skinfold thickness, total cholesterol or triglycerides at the time of their childhood examinations. Beginning in 1996, Cohort members were invited to return for a clinic examination and an ultrasound examination for measurement of IMT. Collected data is provided here from the first EBCT examination for CAC and the first ultrasound examination for IMT, along with risk factor measurements obtained throughout the period of their participation in The Muscatine Study. At the time of the CAC examination, 2 men and 1 woman had been diagnosed with diabetes, and 1 man and 3 women were taking lipid-lowering medications. None of these individuals had evidence of coronary artery calcium.

Measurement of Coronary Artery Calcium (CAC)

Calcium examinations for the 866 cohort members were performed using an Imatron C-150 ultrafast electron beam computed tomographic (EBCT) scanner (Imatron, South San Francisco, Calif.) as previously described (Mahoney et al., J Am Coll Cardiol 27:277-84 (1996)). Briefly, 40 contiguous 3 mm slices were acquired during a single breath hold. Total radiation dose to the skin was estimated to be 10 mGy (1.0 rad). For this analysis, CAC was defined as a focus located within 5 mm of the arterial midlines, with at least 3 contiguous pixels (area 1.03 $mm^2$) having a density of at least 130 Hounsfield units. Image-processing software computed the area of all pixels meeting these criteria within the regions of interest. For the analyses reported here, only the presence or absence of CAC was evaluated, because of the relatively low prevalence of CAC in this age group. Subjects with duplicate scans (approximately 50% of the cohort members) were classified as having CAC if either scan was positive.

Measurement of Carotid Artery Intimal-Medial Thickness (IMT)

Carotid artery ultrasound examination was performed as previously reported (Davis et al., Circulation 104:2815-9 (2001)). For each participant, the maximum carotid IMT was measured for the near and far wall of each common carotid artery, carotid bifurcation, and internal carotid artery. The mean of the maximum carotid IMT measured at the 12 locations (3 sites×2 sides×2 walls) was the variable used for analysis. The mean of non-missing walls was used for participants with missing data for one or more of the 12 locations. Approximately 55% of the participants had a maximum IMT for each of the 12 locations; 35% had a maximum IMT for 9 to 11 of the 12 locations; 98.5% had a maximum IMT for at least 6 of the 12 locations. The minimum number of measurements was 3.

Genotyping

DNA was available for 756 of the 866 cohort members. To genotype the study participants a multilocus allele-specific hybridization assay was used as previously described (Cheng et al., Genome Res. 9:936-49 (1999); Cheng et al., Clin Chem Lab Med 36:561-6 (1998)). Briefly, the first step consisted of a multiplex PCR amplification using a primer blend containing a biotinylated primer pair for each polymorphic site. Next, the biotin-tagged amplification products were hybridized to a linear array of immobilized oligonucleotide probes specific for the alternate alleles of each polymorphic site. Following a stringent wash, chromogenic reagents were used to visualize the biotin-tagged amplicons that remained hybridized. After color development, arrays were scanned for archiving, and genotypes were interpreted by two independent observers.

All genotyping was performed blinded to participant's identity and CAC status. The (−444)A>C polymorphism of $LTC_4S$ corresponds to rs730012. Multilocus genotyping was one successful for 732 (97%) of 100 genetic variants assessed as described in more detail elsewhere [11]. the cohort members; the $LTC_4S$ genotype is available for 725 cohort members.

Primer and Probe Design

Genomic sequence containing the polymorphic site and at least 50 nucleotides on either side of the polymorphism were submitted to the Repeat Masker program (available on the world wide web at repeatmasker.org) to identify and mask repeat sequences such as Alu sequences, short interspersed repeated elements (SINEs), long interspersed repeated elements (LINEs), etc. Masking repeated elements prevents the design of amplification primers within these repeat sequences and minimizes the chances that a primer would anneal non-specifically at multiple locations within the human genome. After masking the DNA, amplifivcation primer sequences were chosen which flank the polymorphic site, and generate an amplicons containing the polymorphic region but do not contain repeat sequences. Exemplary primers include: forward primer—AAGCCAAAGGCACTGGGAAG (SEQ ID NO:01) and reverse primer—ACATCATGCTGGAGC-CAGCC (SEQ ID NO:02). Primers may be designed either manually or by using primer design software. Primers were designed having approximately the same $T_m$, such as 56° C.

Allele-specific oligonucleotide (ASO) hybridization probe sequences corresponding to each alternate allele were chosen by selecting approximately 10 nucleotides to either side of the polymorphic site with the polymorphic nucleotide at approximately the center of the sequence. The probe sequences may be chosen from either strand of the DNA. The probes were designed having approximately the same $T_m$, such as 56° C. Exemplary probes include: Allele 1—GGATGGGGA-CAGGGAACAGAT (SEQ ID NO:03), and Allele 2—GATGGGGACCGGGAACAGAT (SEQ ID NO:04).

Statistical Analysis

Hardy-Weinberg equilibrium was tested using the chi-square goodness-of-fit test with exact p-values determined by a Monte Carlo permutation procedure. The risk factor data collected since childhood were standardized by age, gender and survey year to obtain z scores. These z scores were used to calculate a "risk factor load" which is a time-weighted average z score that utilizes all of the longitudinal measurements available for a given risk factor for each participant. For example, pack years of smoking can be considered to be the smoking "load."

Student's t-test and the nonparametric Wilcoxon rank-sum test were used to compare mean risk factor levels between men and women with (CAC+) and without (CAC−) coronary artery calcium. The tests gave consistent results in terms of statistical significance, and therefore the p-values associated with the t test are reported. Pearson chi-square statistics were computed to compare the genotype distributions among participants with and without CAC.

The goal of the main analysis was to assess the $LTC_4S$(−444)A>C genetic polymorphism for association with CAC and IMT, after adjustment for recognized cardiovascular risk factors (CRFs). The results presented here only relate to the analysis of LCT4S. CRF predictor variables considered for inclusion in prediction models were these risk factor loads: total cholesterol, high-density lipoprotein cholesterol, low-density lipoprotein cholesterol, Apo A1, Apo B, triglycerides, total cholesterol/high-density lipoprotein cholesterol, systolic blood pressure, diastolic blood pressure, waist/hip circumference, and pack years of smoking.

Logistic regression analysis was used to evaluate $LTC_4S$ (−444)A>C for its association with age-risk factor-adjusted odds of CAC. The presence or absence of CAC was assigned as the dependent variable. Receiver operating characteristic (ROC) curves were computed and the area (c) under the ROC curve is reported for each logistic model. A general linear model was fitted to compare age-risk factor-adjusted least squares genotype-specific mean carotid IMT. All analyses were conducted using procedures from the Statistical Analysis System (SAS, version 9.1).

EXAMPLE

Association between Leukotriene $C_4$ Synthase Gene Promoter Polymorphism and Coronary Artery Calcium In an effort to identify those individuals at greater risk for cardiovascular disease (CVD), members of the Muscatine Study Longitudinal Adult Cohort were genotypes for candidate genetic markers associated with several pathogenetic processes, including inflammation. The study identified a gender-specific, age-adjusted increased risk for the (−444) A>C promoter region polymorphism of $LTC_4S$ (OR=4.29; 95% CI 1.78, 10.31) in women. This increased risk is comparable to that associated with elevated levels of established CVD risk factors in the Muscatine Study.

At the time of the EBCT examination to assess CAC, the 341 men with genotype data ranged in age from 29 to 37 years; the 391 women ranged in age from 29 to 43 years. The wider age range for women was by design because the prevalence of calcium among women 29 to 37 years of age is considerably lower than in men. One hundred one (13.8%) of the 732 cohort members with genotype data had evidence of CAC (20.5% of men and 7.9% of women). Among the women, 6% of those 29 to 37 years of age had CAC, compared to 16% of those 40 to 43 years of age.

The distribution of $LTC_4S$ (−444)A>C genotypes was consistent with Hardy-Weinberg expectations; $\chi^2$=0.55 (p>0.40) for men and women combined (p>0.10 for women; p>0.60 for men). Table 1 shows the $LTC_4S$ genotype distribution by CAC status for men and women. $LTC_4S$ shows a strong association with CAC status for women, with 77% of the women with CAC having at least one copy of the variant allele compared to 46% of the women without CAC.

TABLE 1

Distribution of $LTC_4S$ Genotypes in Women and Men with (CAC+) and without (CAC−) Coronary Artery Calcium.

| | CAC− (n/%) | | | CAC+ (n/%) | | | p-value |
|---|---|---|---|---|---|---|---|
| | AA | AC | CC | AA | AC | CC | CAC− vs. CAC+ |
| Women | 191 | 144 | 21 | 7 | 22 | 2 | |
| | 54% | 40% | 6% | 23% | 71% | 6% | <0.005 |
| Men | 133 | 110 | 26 | 30 | 31 | 8 | |
| | 49% | 41% | 10% | 43% | 45% | 12% | >0.60 |

By comparing risk factor levels for men and women and their CAC status, it found that those with CAC tend to be slightly older, with lower HDL-cholesterol, higher systolic and diastolic blood pressures, and higher body mass indices. Table 2 shows several logistic regression models for women that include an indicator variable for $LTC_4S$ (at least one copy of the C allele vs. AA homozygotes), along with age at the time of the EBCT examination and risk factor loads. The odds ratios associated with BMI Load, DBP Load and Apo A1 Load represent one z-score unit, e.g., participants whose BMI Load was 1.0, i.e., one standard deviation above the age-gender-survey specific mean throughout their lifetime, relative to participants whose BMI Load was 0.0, i.e., at the age-gender-survey specific-mean throughout their lifetime. Apo A1 was not measured until the Young Adult Follow-up examinations.

TABLE 2

Logistic Regression Models of the Association between Coronary Artery Calcium Status and Risk Factor Loads, and LTC$_4$S Genotypes in Women.

|  | Model 1 | Model 2 | Model 3 | Model 4 | Model 5 |
|---|---|---|---|---|---|
| V1 CAC Age | 1.16 (1.05, 1.28)* <0.005 | 1.18 (1.07, 1.31) <0.0025 | 1.18 (1.06, 1.31) <0.0025 | 1.19 (1.08, 1.33) <0.001 | 1.20 (1.08, 1.33) <0.001 |
| BMI Load | — | 2.64 (1.73, 4.04) <0.0001 | 2.26 (1.44, 3.55) <0.0005 | 2.53 (1.64, 3.92) <0.0001 | 2.11 (1.33, 3.34) <0.0025 |
| DBP Load | — | — | 1.90 (1.02, 3.53) <0.05 | — | 2.16 (1.15, 4.06) <0.025 |
| Apo A1 | — | — | — | 0.57 (0.34, 0.97) <0.05 | 0.51 (0.29, 0.88) <0.025 |
| LTC$_4$S | 4.29 (1.78, 10.31) <0.0025 | 5.21 (2.05, 13.26) <0.0005 | 6.64 (2.45, 18.02) <0.0005 | 5.04 (1.98, 12.82) <0.001 | 6.81 (2.49, 18.68) <0.0005 |
| n | 387 | 387 | 387 | 386 | 386 |
| c | 0.716 | 0.795 | 0.825 | 0.818 | 0.851 |

*Odds Ratio (95% Confidence Interval), p-value
— indicates that the variable was not included in the model
DBP = diastolic blood pressure
BMI = body mass index The first model indicates that women with at least one copy of the variant C allele at the LTC$_4$S locus had increased age-adjusted odds of CAC relative to those with the AA genotype of 4.29 (95% CI 1.78, 10.31). Three of the load variables were also consistently significant in the logistic models: body mass index, diastolic blood pressure, and Apolipoprotein A1. Models 2 through 5 show the results from inclusion of various combinations of these three risk factor loads. The genotype-specific odds ratios are greater than those of Model 1, indicating that the associations identified between the LTC$_4$S genotype and CAC in women are not explained by an association between LTC$_4$S and any of these recognized cardiovascular risk factors. The age-BMI load-DBP load-Apolipoprotein A1 load-adjusted odds of CAC are almost 7-fold higher for women who carry at least one LTC$_4$S C allele relative to women who are AA homozygotes.

Finally, because carotid IMT was available for these women from an examination four to five years after the EBCT examination, the association between the LTC$_4$S and mean carotid IMT was also investigated. Table 3 displays age-risk factor-adjusted LTC$_4$S genotype-specific least squares means from a general linear models analysis. For this LTC$_4$S polymorphism, women with at least one copy of the C allele have significantly higher (p<0.0025) adjusted mean carotid IMT when compared to women who are AA homozygotes. Based on measurements that assess the early atherosclerotic process in two different vascular beds, the results show a significant association between LTC$_4$S and subclinical disease in women in The Muscatine Study.

TABLE 3

Association between LTC$_4$S and Carotid Artery Intimal-Medial Thickness in Women (n = 371).

| Predictor Variable | p-value |
|---|---|
| IMT age | <0.0025 |
| Systolic BP Load | <0.01 |
| Cholesterol Load | <0.01 |
| Chol/HDL Load | <0.05 |
| BMI Load | <0.10 |
| LTC$_4$S C allele | <0.0025 |

| LTC$_4$S Genotype | Least Squares Mean ± SE |
|---|---|
| AA | 0.702 ± 0.007 |
| AC and CC | 0.733 ± 0.007 |

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of determining a predisposition to atherosclerosis in a female human subject, said method comprising:
   assaying the promoter region of leukotriene C4 synthase (LTC4S) in a biological sample of the subject;
   detecting the presence of a cytosine at position −444 in said promoter region; and
   determining a predisposition to atherosclerosis based on said presence of said cytosine.

2. The method of claim 1, wherein the assaying comprises a polymerase chain reaction.

3. The method of claim 1, wherein the assaying comprises hybridization.

4. The method of claim 2, wherein the assaying further comprises sequencing of the product of the polymerase chain reaction.

5. A method of determining predisposition for the presence of Coronary Artery Calcium (CAC) in a female human subject comprising:
   assaying the promoter region of leukotriene C4 synthase (LTC4S) in a biological sample of the subject;
   detecting the presence of a cytosine at position −444 in said promoter region; and
   determining the predisposition for the presence of CAC in the subject based on said presence of said cytosine.

6. The method of claim 5, wherein the assaying comprises a polymerase chain reaction.

7. The method of claim 6, wherein the assaying further comprises sequencing of the product of the polymerase chain reaction.

8. The method of claim 5, wherein the assaying comprises hybridization.

9. A method of determining a predisposition to atherosclerosis in a female human subject comprising:
- assaying the promoter region of leukotriene C4 synthase (LTC4S) in a biological sample from the subject;
- detecting the presence of a cytosine at position −444 in said promoter region; and
- determining predisposition to a high mean carotid artery intimal-medial thickness in the subject based on said presence of said cytosine wherein high mean carotid artery intimal-medial thickness indicates a predisposition to atherosclerosis.

10. The method of claim 9, wherein the assaying comprises a polymerase chain reaction.

11. The method of claim 10, wherein the assaying further comprises sequencing of the product of the polymerase chain reaction.

12. The method of claim 9, wherein the assaying comprises hybridization.

* * * * *